United States Patent
Garino

(10) Patent No.: US 10,610,274 B2
(45) Date of Patent: Apr. 7, 2020

(54) INSTRUMENT FOR FRACTURE ALIGNMENT AND PLATE COMPRESSION

(71) Applicant: Jonathan P. Garino, Villanova, PA (US)

(72) Inventor: Jonathan P. Garino, Villanova, PA (US)

(*) Notice: Subject to any disclaimer, the term of this patent is extended or adjusted under 35 U.S.C. 154(b) by 0 days.

(21) Appl. No.: 15/906,490

(22) Filed: Feb. 27, 2018

(65) Prior Publication Data

US 2019/0262045 A1  Aug. 29, 2019

(51) Int. Cl.
| | |
|---|---|
| *A61B 17/80* | (2006.01) |
| *A61B 17/72* | (2006.01) |
| *A61B 17/74* | (2006.01) |
| *A61B 17/68* | (2006.01) |
| *A61B 17/88* | (2006.01) |
| *A61B 17/00* | (2006.01) |

(52) U.S. Cl.
CPC ........ *A61B 17/8014* (2013.01); *A61B 17/683* (2013.01); *A61B 17/72* (2013.01); *A61B 17/74* (2013.01); *A61B 17/808* (2013.01); *A61B 17/809* (2013.01); *A61B 17/8866* (2013.01); *A61B 17/8872* (2013.01); *A61B 17/8061* (2013.01); *A61B 2017/00367* (2013.01); *A61B 2017/681* (2013.01)

(58) Field of Classification Search
CPC .............. A61B 17/68; A61B 2090/067; A61B 17/8605; A61B 17/1728; A61B 17/8014; A61B 17/74; A61B 17/72; A61B 17/809; A61B 2017/681; A61B 2017/00367; A61B 17/8866; A61B 17/282; A61B 17/8061
See application file for complete search history.

(56) References Cited

U.S. PATENT DOCUMENTS

| | | | |
|---|---|---|---|
| 2,583,896 A | 1/1952 | Siebrandt | |
| 7,488,327 B2 * | 2/2009 | Rathbun | ............ A61B 17/1728 606/96 |
| 7,803,176 B2 * | 9/2010 | Teague | ............... A61B 17/8076 24/309 |

(Continued)

FOREIGN PATENT DOCUMENTS

DE    102009042701 A1    3/2011

OTHER PUBLICATIONS

International Search Report and Written Opinion for International Application No. PCT/US2018/055184, dated Jan. 21, 2019, 12 pages.

*Primary Examiner* — Lynnsy M Summitt
*Assistant Examiner* — Tara Rose E Carter
(74) *Attorney, Agent, or Firm* — RatnerPrestia

(57) ABSTRACT

An instrument and method of using the instrument for setting a fracture in a bone and applying a bone plate to the fractured bone. The instrument includes a connector for connecting the instrument to the intramedullary rod. At least two tines are movably connected to the connector and configured to orient the fractured bone with respect to the rod. Each tine has a distal end configured to contact the bone. At least one plate carrier is configured to receive the bone plate. The at least one plate carrier is movably connected to the connector and configured to move relative to the connector and the tines to position the bone plate adjacent the bone in a predetermined alignment with the intramedullary rod.

22 Claims, 13 Drawing Sheets

(56) References Cited

U.S. PATENT DOCUMENTS

| | | | |
|---|---|---|---|
| 8,152,807 B2* | 4/2012 | Edwards | A61B 17/1725 |
| | | | 606/62 |
| 9,463,053 B2 | 6/2016 | Garino | |
| 2003/0135212 A1* | 7/2003 | Y. Chow | A61B 17/72 |
| | | | 606/64 |
| 2009/0306664 A1 | 12/2009 | Teeny | |
| 2010/0292743 A1* | 11/2010 | Singhal | A61B 17/175 |
| | | | 606/86 R |
| 2019/0000509 A1* | 1/2019 | Cowens | A61B 17/68 |

\* cited by examiner

INSTRUMENT FOR FRACTURE ALIGNMENT AND PLATE COMPRESSION

FIELD OF THE INVENTION

The invention relates to an instrument for aligning a periprosthetic fracture and installing compression plates adjacent the periprosthetic fracture.

BACKGROUND

A common problem associated with joint replacement surgery is the development of fractures around the prosthetic, known as periprosthetic fractures. For example in a Total Knee Replacement (TKR) procedure, fractures may occur in the femur around the prosthetic joint implanted at the distal portion of the femur. Various treatments are employed depending on the severity of the fractures and whether the prosthetic becomes loose. The fractures generally occur as a result of trauma or infection and in extreme cases may require additional surgical procedures in order to re-align the prosthetic knee and/or apply additional plates or rods, so that the fractures will heal properly. In most cases when a periprosthetic knee fracture occurs, the prosthesis remains well fixed to the bone beneath it and securing the bone to the part of the femur which has broken away is a challenge.

Mending such fractures is a challenge due to the lack of available healthy bone remaining around the location of the fractures. As a result, fracture fixation may be inadequate and the fracture may heal incorrectly, causing abnormal stresses on the prosthetic joint, which in turn may cause pain, stiffness, and potential TKR failure. Therefore, there is a need for improved surgical implants to mend periprosthetic fractures, and instruments for applying the improved surgical implants to the periprosthetic fractures. Such an improved surgical implant is disclosed in U.S. Pat. No. 9,463,053 to Garino, which is incorporated by reference herein in its entirety and for all purposes.

SUMMARY OF THE INVENTION

Described herein is an instrument for setting a fracture in a bone and applying a bone plate to the fractured bone and method of using that instrument.

According to an embodiment of the present invention, an instrument for setting a fracture in a bone and affixing a bone plate to the fractured bone with a connection to an intramedullary rod fixed in the fractured bone is described. The instrument includes a connector for connecting the instrument to the intramedullary rod. At least two tines are movably connected to the connector and configured to orient the fractured bone with respect to the rod. Each tine has a distal end configured to contact the bone. At least one plate carrier is configured to receive the bone plate. The at least one plate carrier is movably connected to the connector and configured to move relative to the connector and the tines to position the bone plate adjacent the bone in a predetermined alignment with the intramedullary rod.

According to another embodiment of the present invention, a method of using an instrument to mend a fracture in a bone comprises the steps of:

(i) attaching a connector of the instrument to an intramedullary rod positioned within a cavity of the bone;

(ii) positioning tines of the instrument against the bone;

(iii) moving the tines with respect to the intramedullary rod to orient the fractured bone with respect to the intramedullary rod thereby setting the fracture; and (iv) moving the first plate carrier with respect to the intramedullary rod to position a first plate, which is mounted to the first plate carrier, against a first surface of the bone in alignment with the intramedullary rod.

BRIEF DESCRIPTION OF THE DRAWING FIGURES

Figure 5:
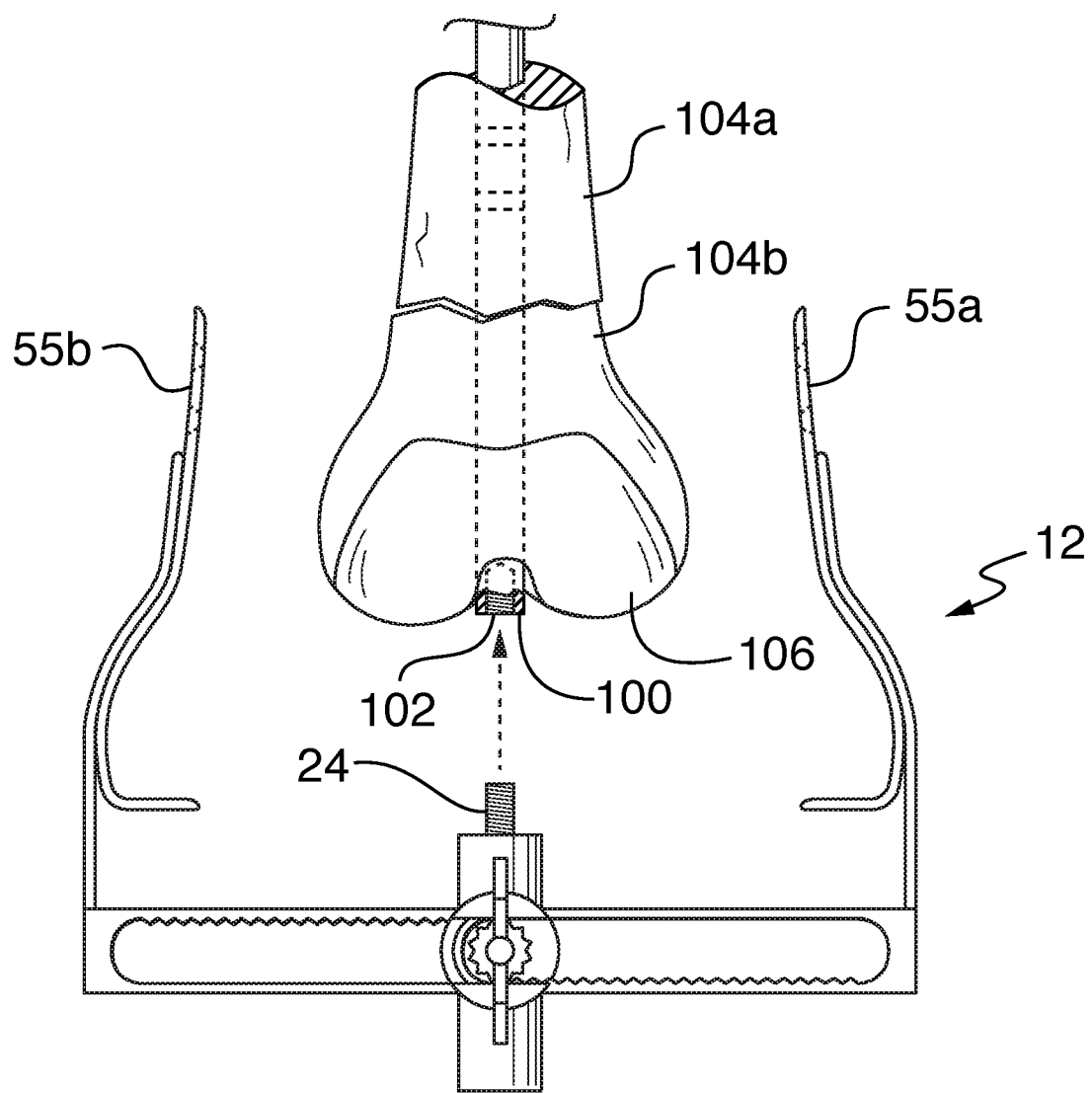
FIGS. 5-12 depicts a process for aligning a fracture and applying plates to the aligned fracture.

Specifically, FIG. 5 depicts the step of aligning a connector on the plate compression portion of the instrument with a rod that is inserted into the femur.

Figure 6:
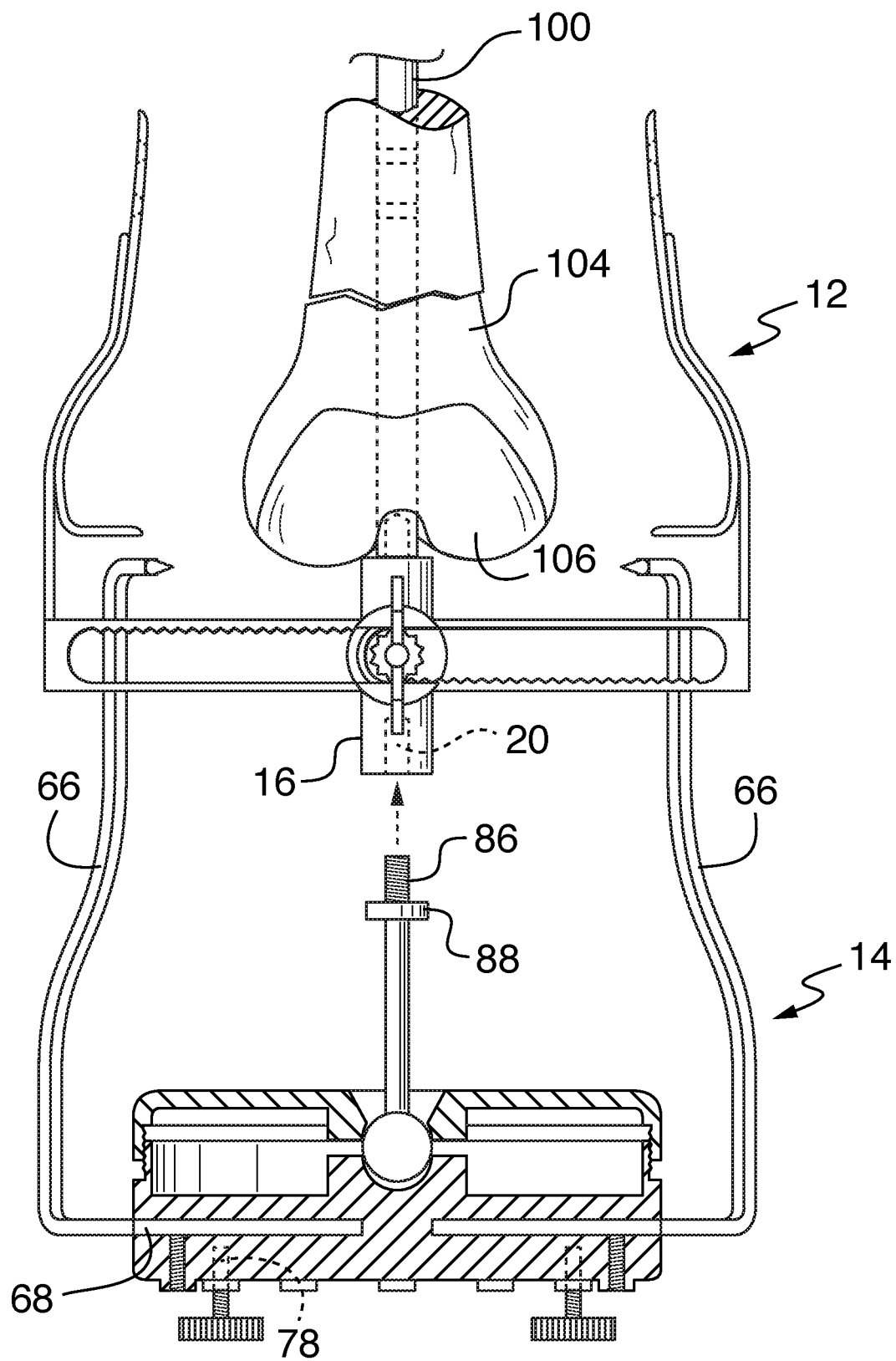

FIG. 6 depicts the step of attaching the plate compression portion of the instrument to the fracture alignment portion of the instrument.

Figure 7:
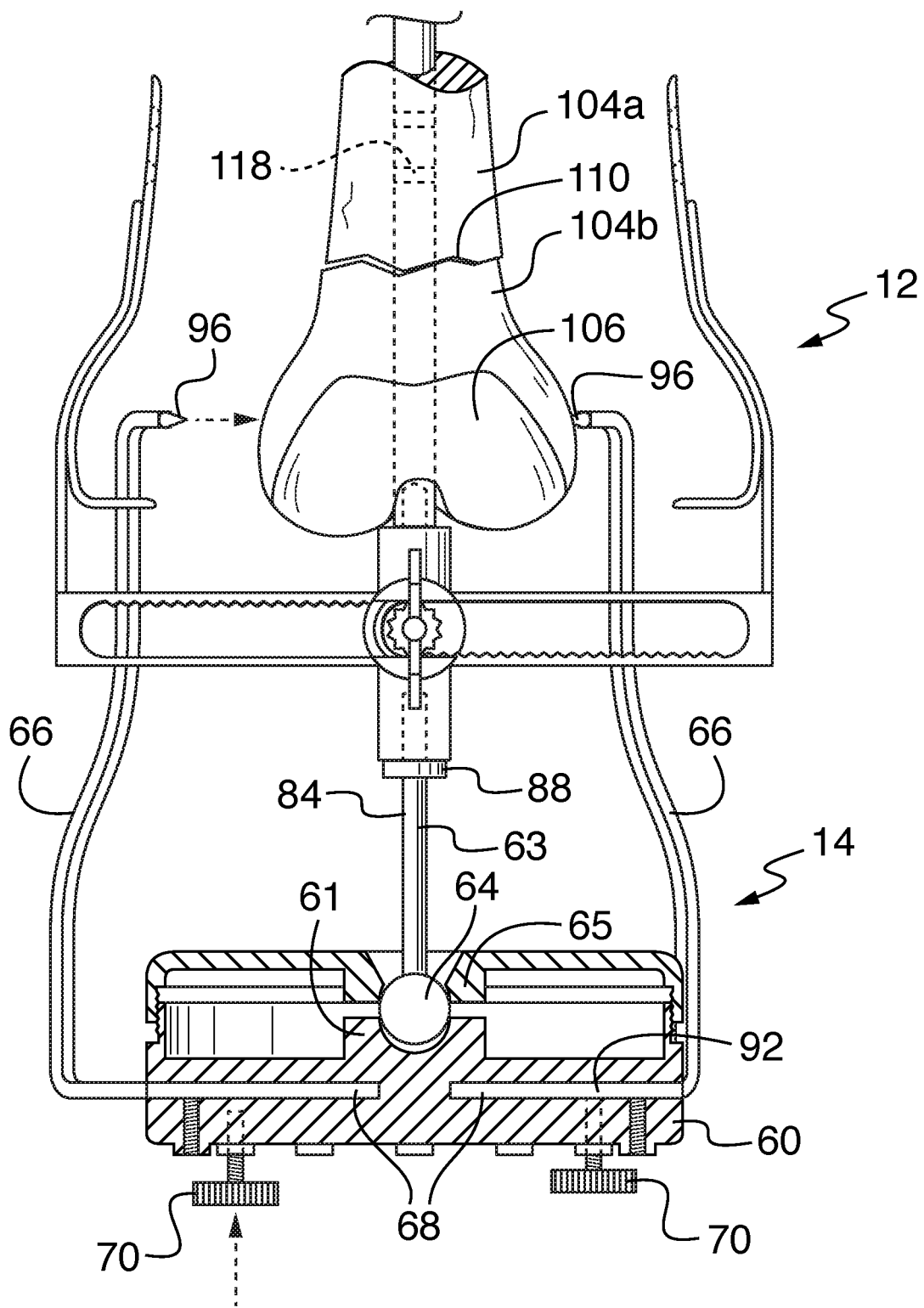

FIG. 7 depicts the step of positioning the fracture alignment portion of the instrument against the fracture.

Figure 8:
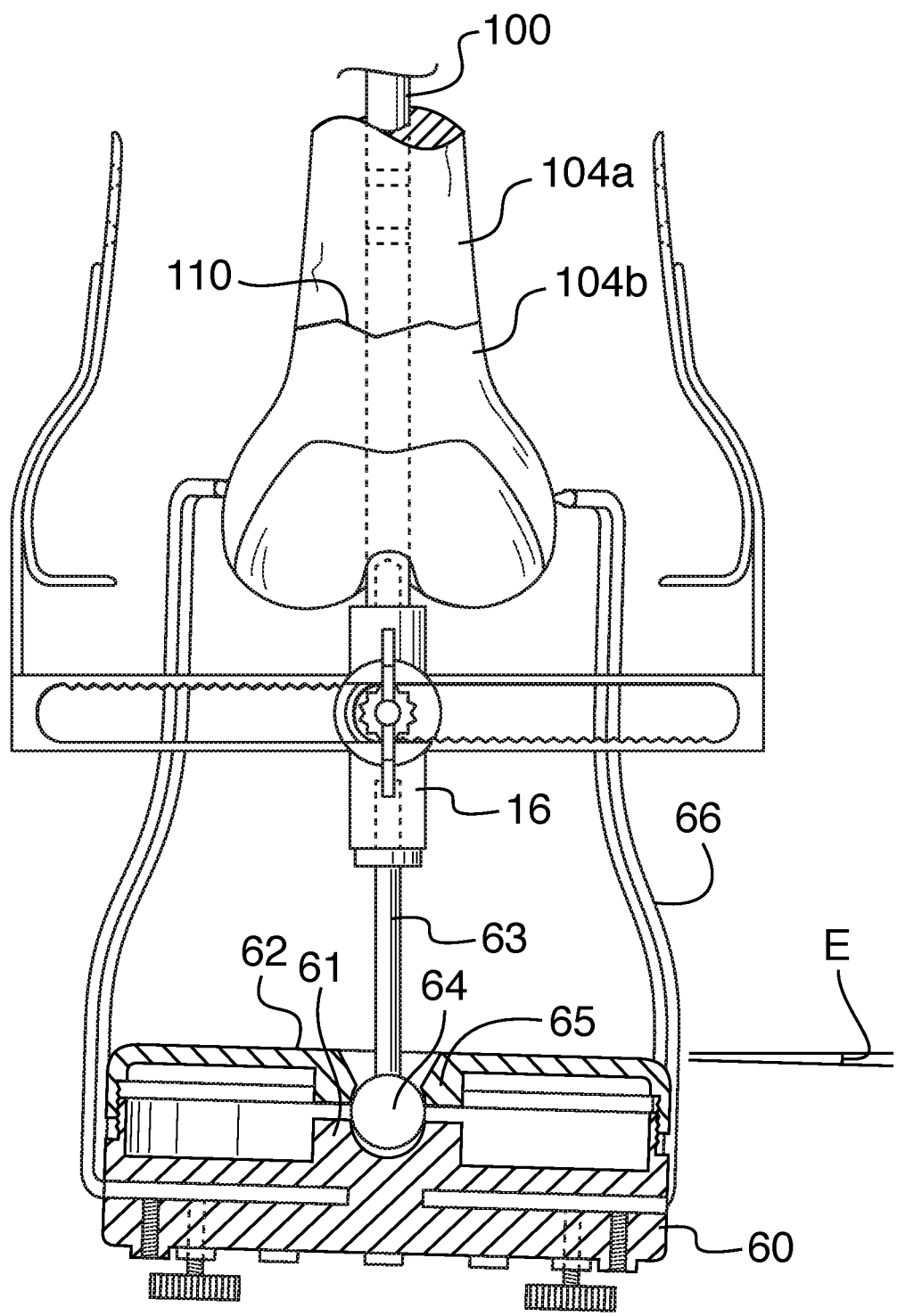

FIG. 8 depicts the step of aligning the fracture using the fracture alignment portion of the instrument.

Figure 9:
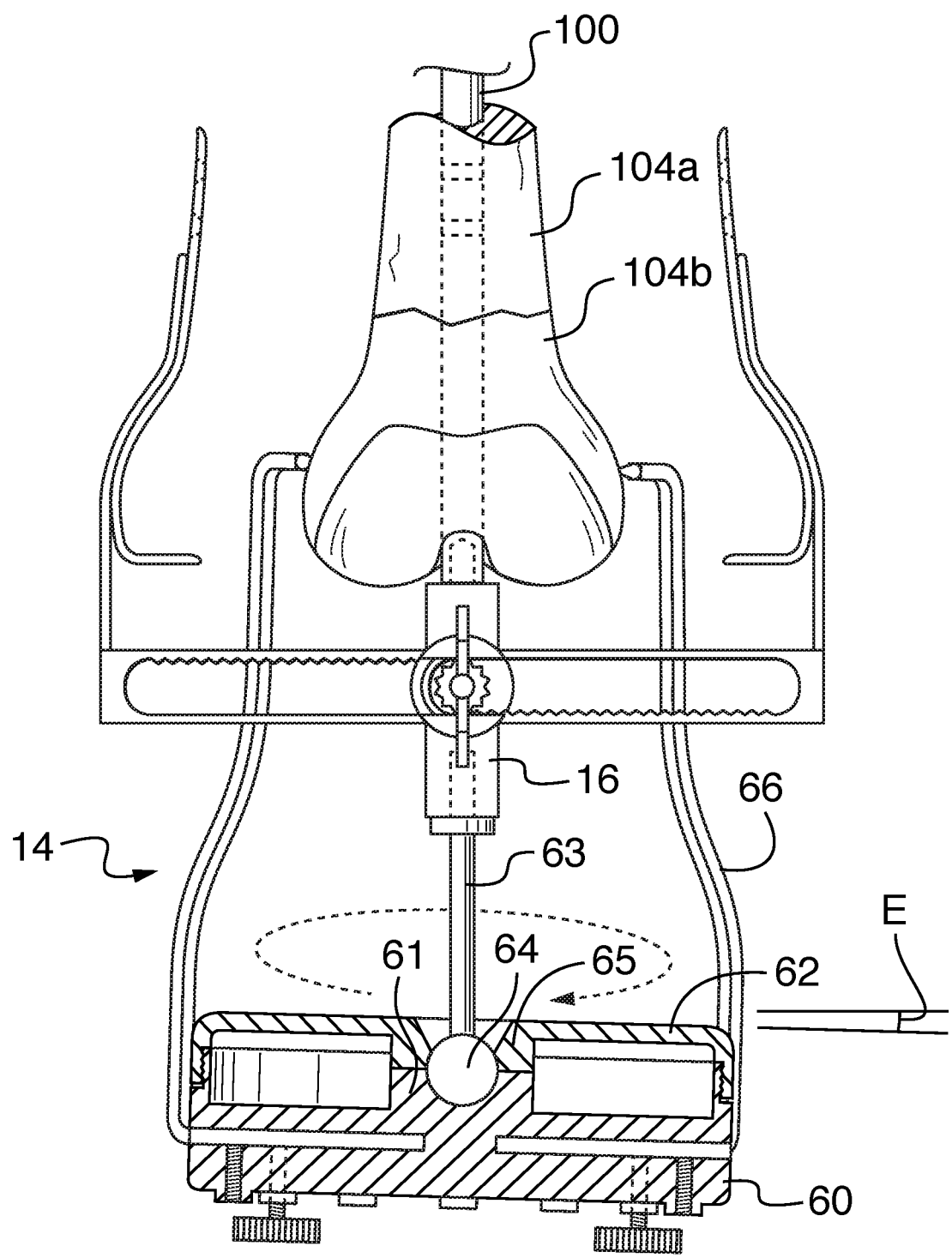

FIG. 9 depicts the step of locking the fracture alignment portion of the instrument so that the fracture alignment portion remains stationary with respect to the plate compression portion of the instrument.

Figure 10:
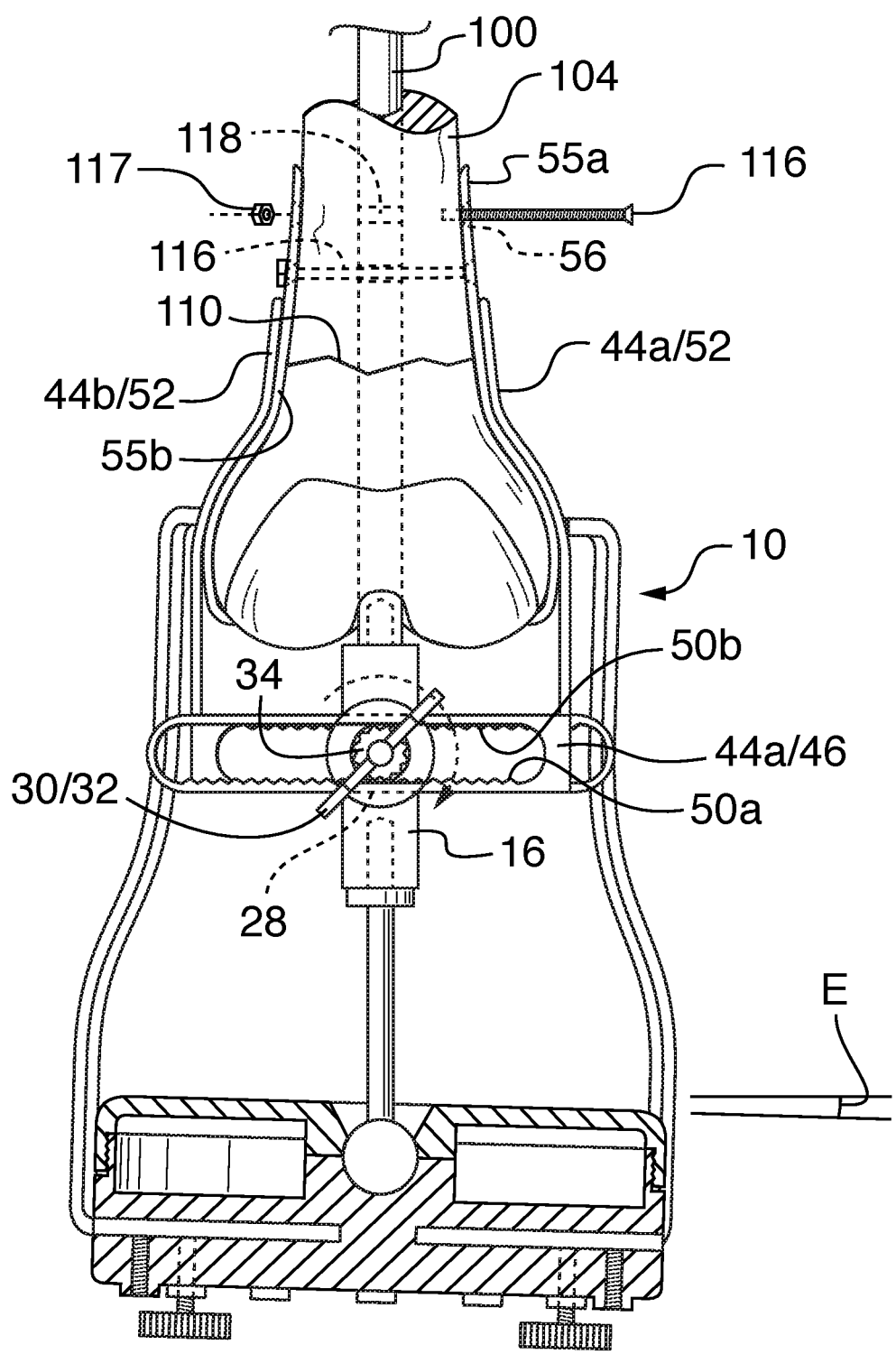

FIG. 10 depicts the steps of applying the compression plates against the fracture and delivering fasteners through the plates, the rod and the bone.

Figure 11:
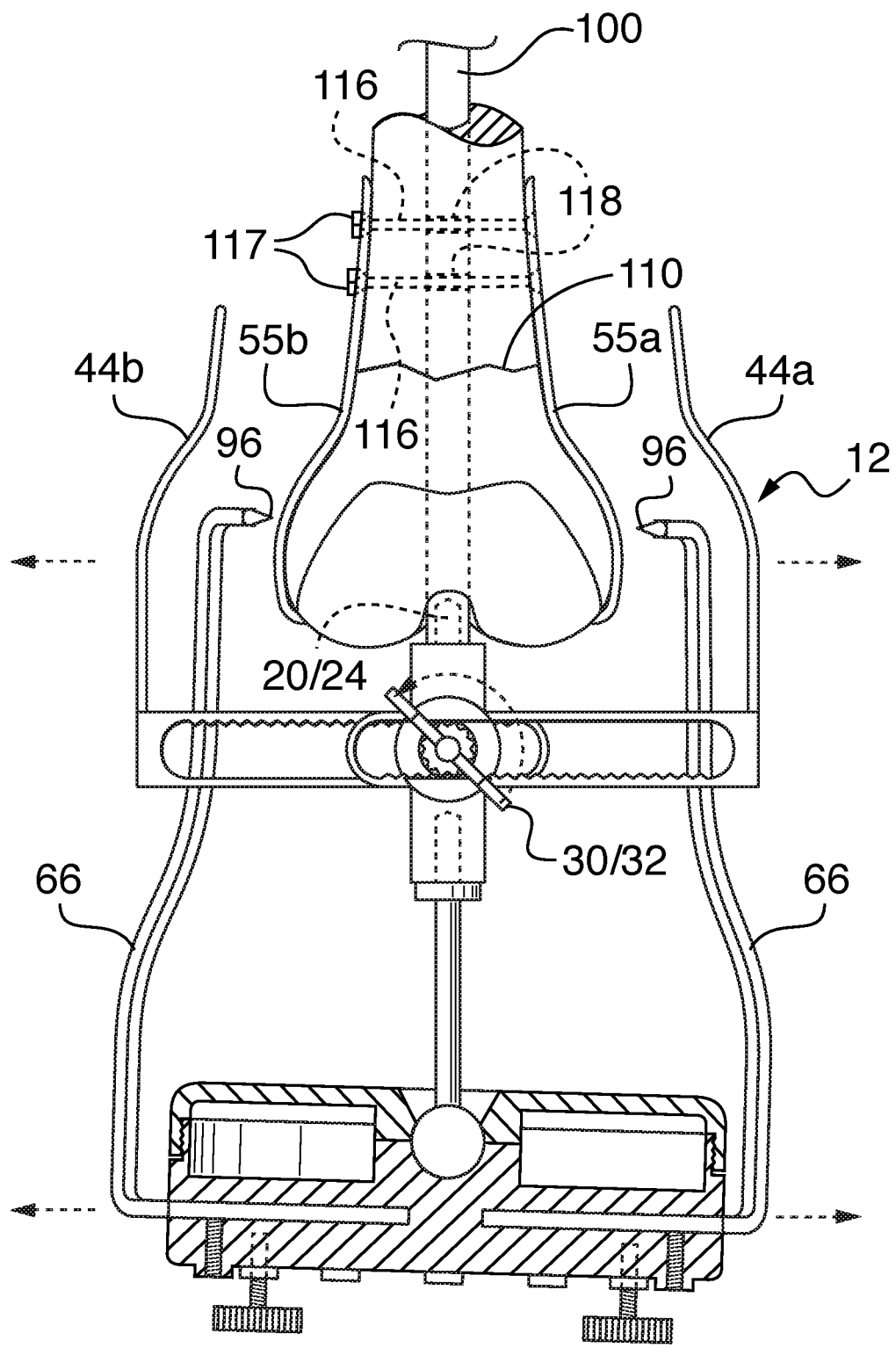

FIG. 11 depicts the step of releasing the instrument from the bone and the plates.

Figure 12:
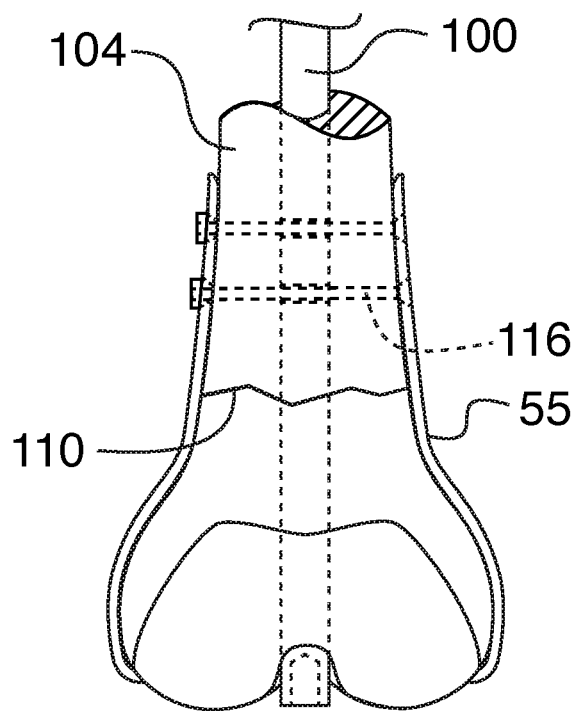

FIG. 12 depicts the bone having plates applied thereto.

Figure 1:
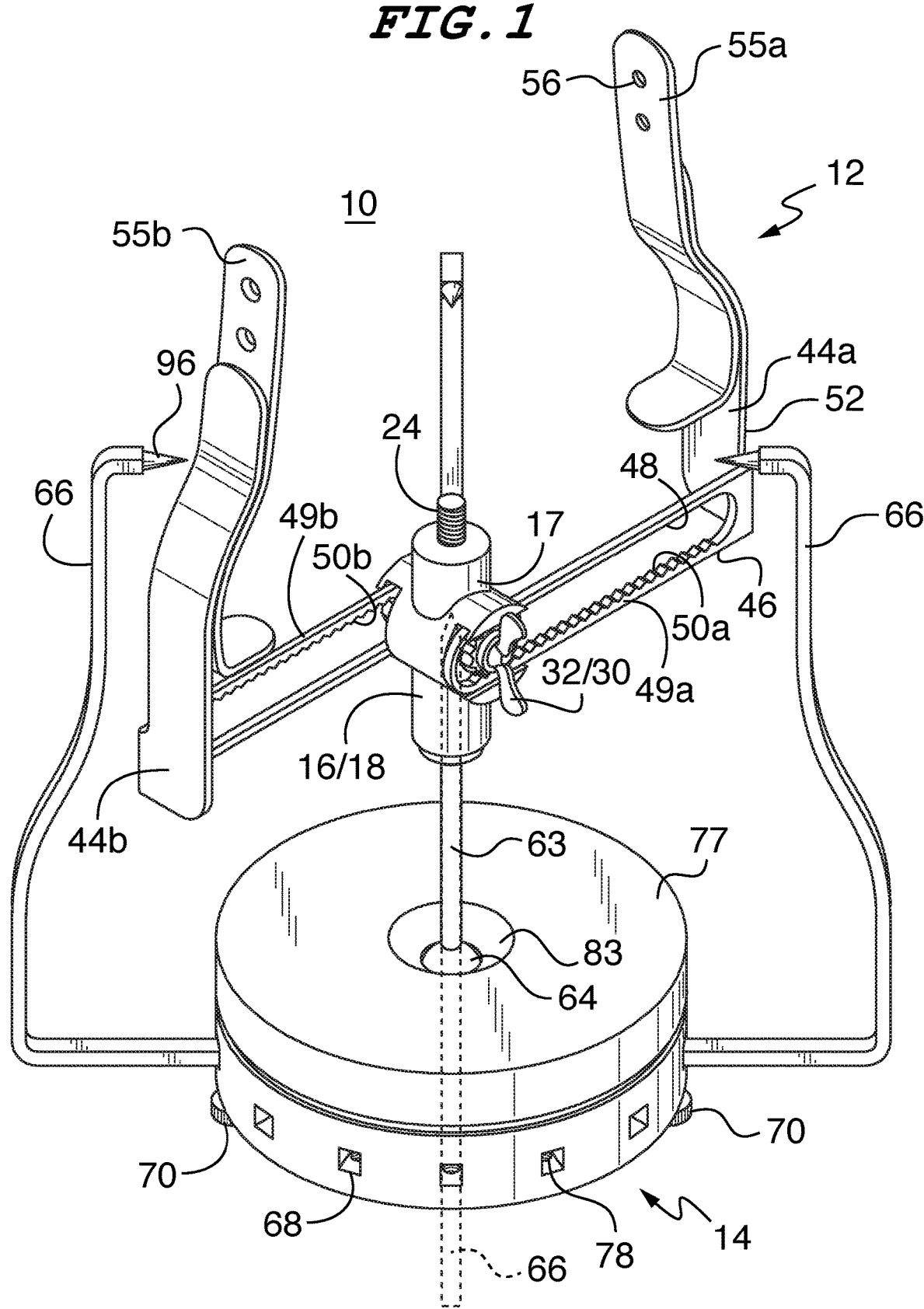
FIG. 1 is an isometric view of an instrument for plate compression and fracture alignment, according to one exemplary embodiment of the invention.
Figure 13:
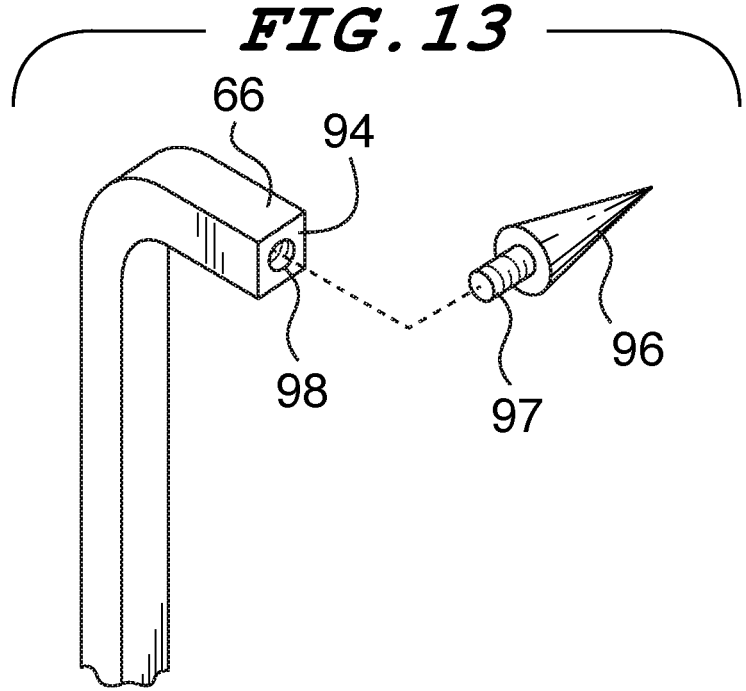

FIG. 13 depicts an exploded view of a tine of the instrument of FIG. 1.

Figure 14:
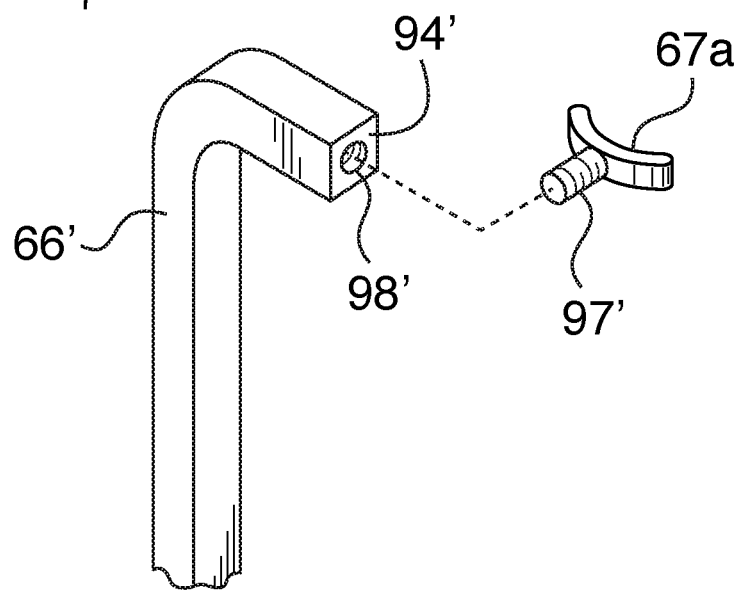

FIG. 14 depicts an exploded view of a tine according to another embodiment.

Figure 15:
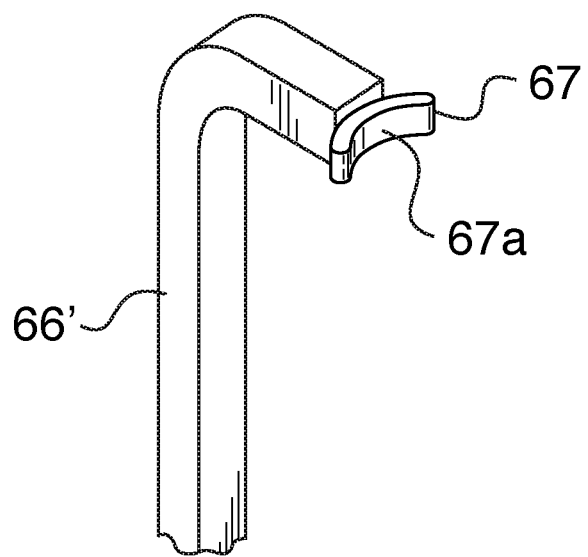

FIG. 15 depicts the assembled tine of FIG. 14.

DETAILED DESCRIPTION OF THE INVENTION

The invention will now be described by reference to exemplary embodiments and variations of those embodiments. Although the invention is illustrated and described herein with reference to specific embodiments, the invention is not intended to be limited to the details shown and described. Rather, various modifications may be made in the details within the scope and range of equivalents of the claims and without departing from the invention.

FIGS. 1-5 depict an exemplary embodiment of an instrument 10 (or portions thereof) for fracture alignment and plate compression, according to one exemplary embodiment of the invention. The instrument 10 generally includes a plate compression portion 12 that is releasably connected to a fracture alignment portion 14. While the portions 12 and 14 may be releasably connected together, it should be understood that those portions 12 and 14 may be permanently connected together.

Figure 2:
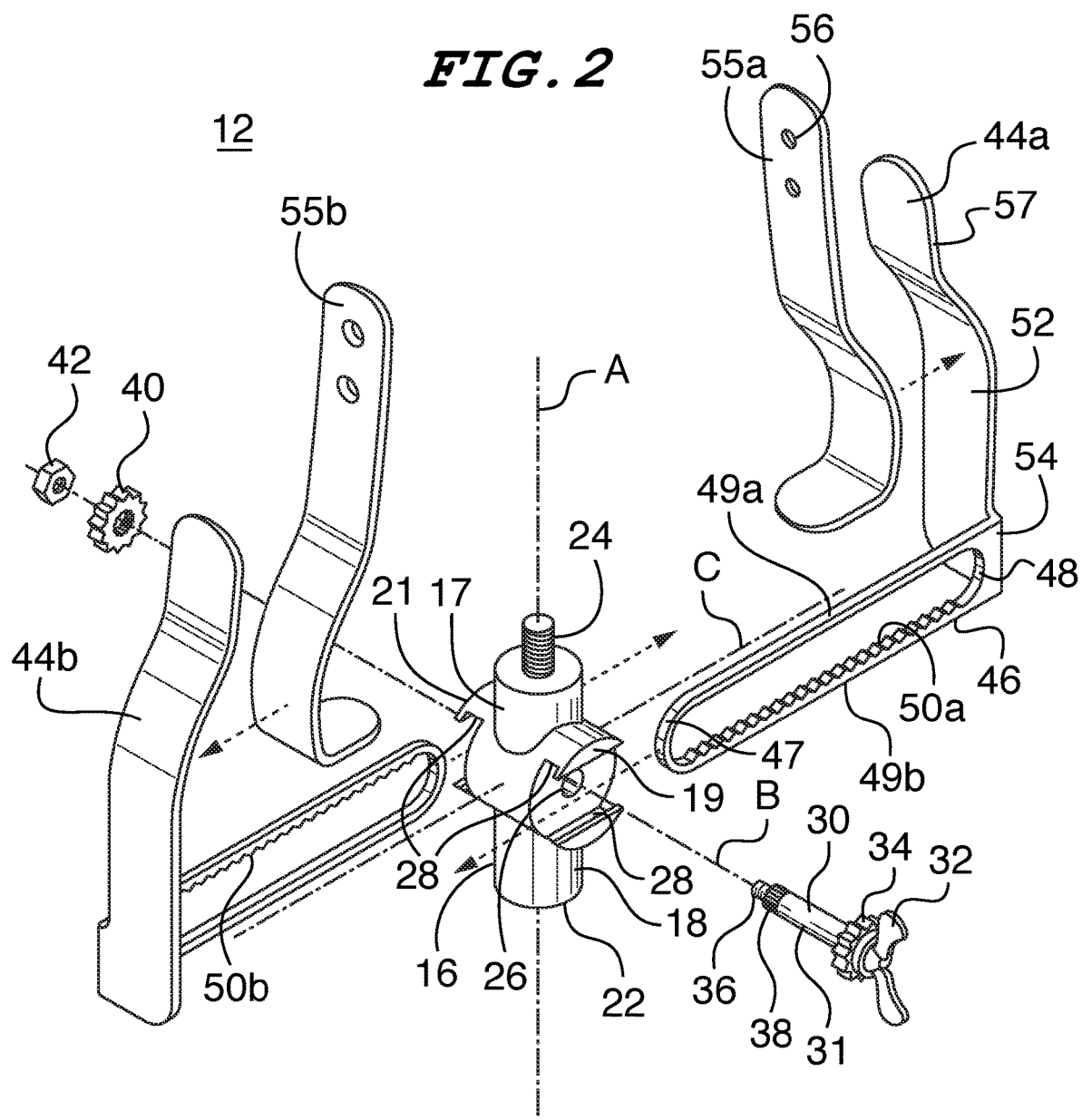
FIG. 2 is an exploded view of a plate compression portion of the instrument of FIG. 1.
Figure 4:
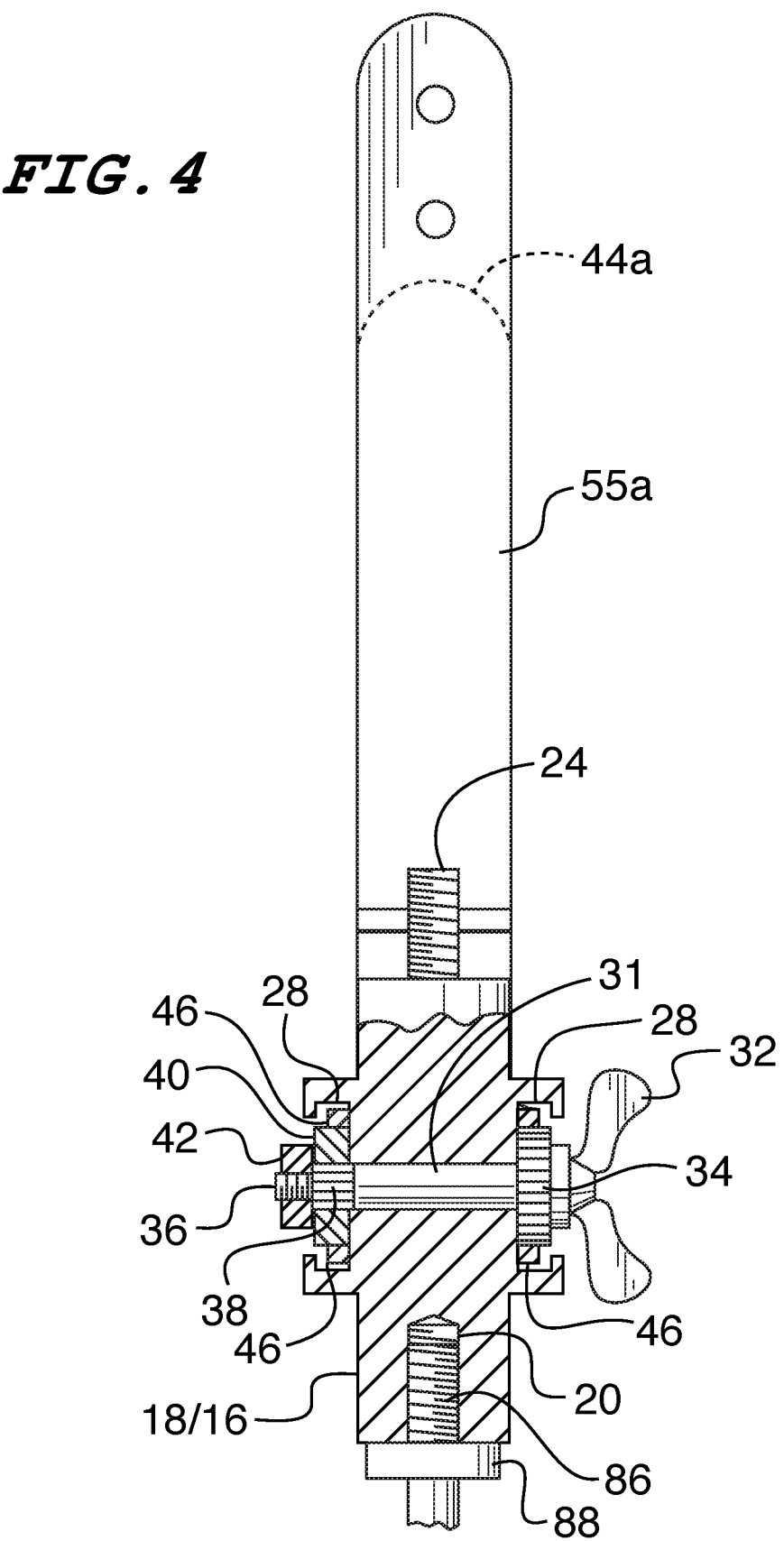
FIG. 4 is a partial cross-sectional view of the instrument of FIG. 1.

The plate compression portion 12, which is best shown in FIGS. 2 and 4, generally comprises a four-way connector 16 having a t-shaped body extending along a longitudinal axis A and a transverse axis B oriented orthogonally from the longitudinal axis A. The components of the instrument 10 are mounted either directly or indirectly to the four-way connector 16.

As best shown in FIG. 2, the four-way connector 16 comprises a point of intersection where the axes A and B intersect. An upper cylindrical shaft 17 extends upwardly from the point of intersection along axis A, a lower cylindrical shaft 18 extends downwardly from the point of intersection along axis A, a slotted shaft 19 extends laterally from one side of the connector 16 along axis B, and another slotted shaft 21 extends laterally from an opposing side of the connector 16 along axis B. A third axis C intersects axes A and B and is normal to both axes A and B.

A blind threaded hole 20 (FIG. 4) is disposed on the lower surface 22 of the shaft 18 and centered on the shaft 18 through axis A. A threaded post 24 extends upwardly from the top end of the upper cylindrical shaft 17 and is centered on the shaft 17 through axis A. A thru-hole 26 extends through the shafts 19 and 21 is aligned with axis B. A rectangular four-wall channel 28 is defined at the free end of each shaft 19 and 21. The longitudinal axis of each channel 28 is parallel to axis C, and intersects and is normal to the axis B.

A fastener 30 is positioned through the hole 26 in the connector 16. The fastener 30 includes an elongated shaft 31. A pair of wings 32, or other manipulable feature, is provided at the proximal end of the shaft 31. Those of ordinary skill in the art will recognize that the proximal end of the shaft 31 may have a variety of head types, such as Phillips, slotted, hex, etc. that can be used for rotating the shaft 31. A gear 34 having teeth on its outer perimeter is disposed on the proximal end of the shaft directly adjacent the wings 32. The gear 34 is non-rotatably connected to the shaft 31. The gear 34 may be integrally formed on the shaft 31, or, alternatively, the gear 34 may be non-rotatably connected to the shaft 31 by a toothed interface (like that of gear 40). The distal tip 36 of the shaft 31 is threaded. A toothed region 38 is defined on the distal end of the shaft 31 at a location proximal of the distal tip 36.

A gear 40 has a toothed surface on its outer perimeter, and a toothed surface on its inner perimeter. The teeth on the inner perimeter of the gear 40 are meshed with the toothed region 38 of the fastener 30 so that the gear 40 rotates along with the fastener 30. A threaded hex nut 42 is configured to be threadedly connected to the threaded distal tip 36 of the fastener 30, thereby captivating the fastener 30, the gear 34, the gear 40 and the connector 16 together.

Two plate carriers 44a and 44b are slidably connected to the connector 16. The plate carriers 44a and 44b are similar and may be referred to either individually or collectively as plate carrier(s) 44. Each plate carrier 44 includes an L-shaped body. The L-shaped body includes a first elongated portion 46 that extends parallel to axis C. The first elongated portion 46 has a substantially rectangular shape with a rounded edge 47 at its free end. An elongated recess 48 is defined within the first elongated portion 46, thereby defining a top rail 49a and a bottom rail 49b on the portion 46.

In the plate carrier 44a, a set of teeth 50a extend along the interior side of the bottom rail 49b. In the plate carrier 44b, a set of teeth 50b extend along the interior side of the top rail 49a. The teeth 50a of the plate carrier 44a mesh with the outer teeth of the gear 34, whereas the teeth 50b of the other plate carrier 44b mesh with the outer teeth of the gear 40.

A second elongated portion 52 of each plate carrier 44 vertically depends from the first elongated portion 46. The portion 52 extends substantially parallel to axis A and orthogonal to portion 46. The portion 52 meets the portion 46 at a ninety degree bend 54 in the plate carrier 44. The distal end 57 of the second elongated portion 52 is bent inwardly towards the connector 16 (in an assembled form of the instrument). The second elongated portion 52 is shaped to compliment the shape of the plate 55 that is connected to the plate carrier 44.

A plate 55 is mounted to each plate carrier 44 by a clip, fastener, magnet, connector, channel or other mounting surface, for example, or any other means for mounting that is known to those skilled in the art. Specifically, plate 55a is mounted to plate carrier 44a, and plate 55b is mounted to plate carrier 44b. The plates 55 are substantially identical. The plates 55 are configured to be mounted to a bone for securing a periprosthetic fracture in that bone. A series of holes 56 are defined in the plate 55.

Although each plate 55 is shown having two holes 56 at its top end, the pattern of holes 56 may continue along the entire length of the plate 55. Also, if the plate 55 includes more than the holes 56 that are shown, a pattern of holes (not shown) may be disposed in the plate carrier 44, such that the holes in the plate carrier 44 will register with the holes in the plate 55. Further details of the plate 55 are described in U.S. Pat. No. 9,463,053 to Garino, which is incorporated by reference herein in its entirety and for all purposes.

In an assembled form of the plate compression portion 12, the first elongated portion 46 of the plate carrier 44a is mounted in the channel 28 of the shaft 19, the first elongated portion 46 of the plate carrier 44b is mounted in the channel 28 of the shaft 21, and the shaft 31 of the fastener 30 is positioned through the hole 26 in the connector 16. The gear 34 is positioned within the channel 28 of the connector shaft 19 and the teeth of the gear 34 are meshed with the teeth 50a of the plate carrier 44a. The gear 40 is mounted to the distal end of the shaft 31 and the internal teeth of the gear 40 are meshed with the teeth 38 of the shaft 31. The gear 40 is positioned within the channel 28 of the connector shaft 21 and the outer teeth of the gear 40 are meshed with the teeth 50b of the plate carrier 44b. The threaded hex nut 42 is threadedly connected to the threaded distal tip 36 of the fastener 30, thereby connecting the gear 34, the gear 40, the connector 16 and the fastener 30 together. The plates 55 are releasably mounted to respective plate carriers 44a and 44b by any means known in the art, such as a clip, clamp or fastener.

Figure 3:
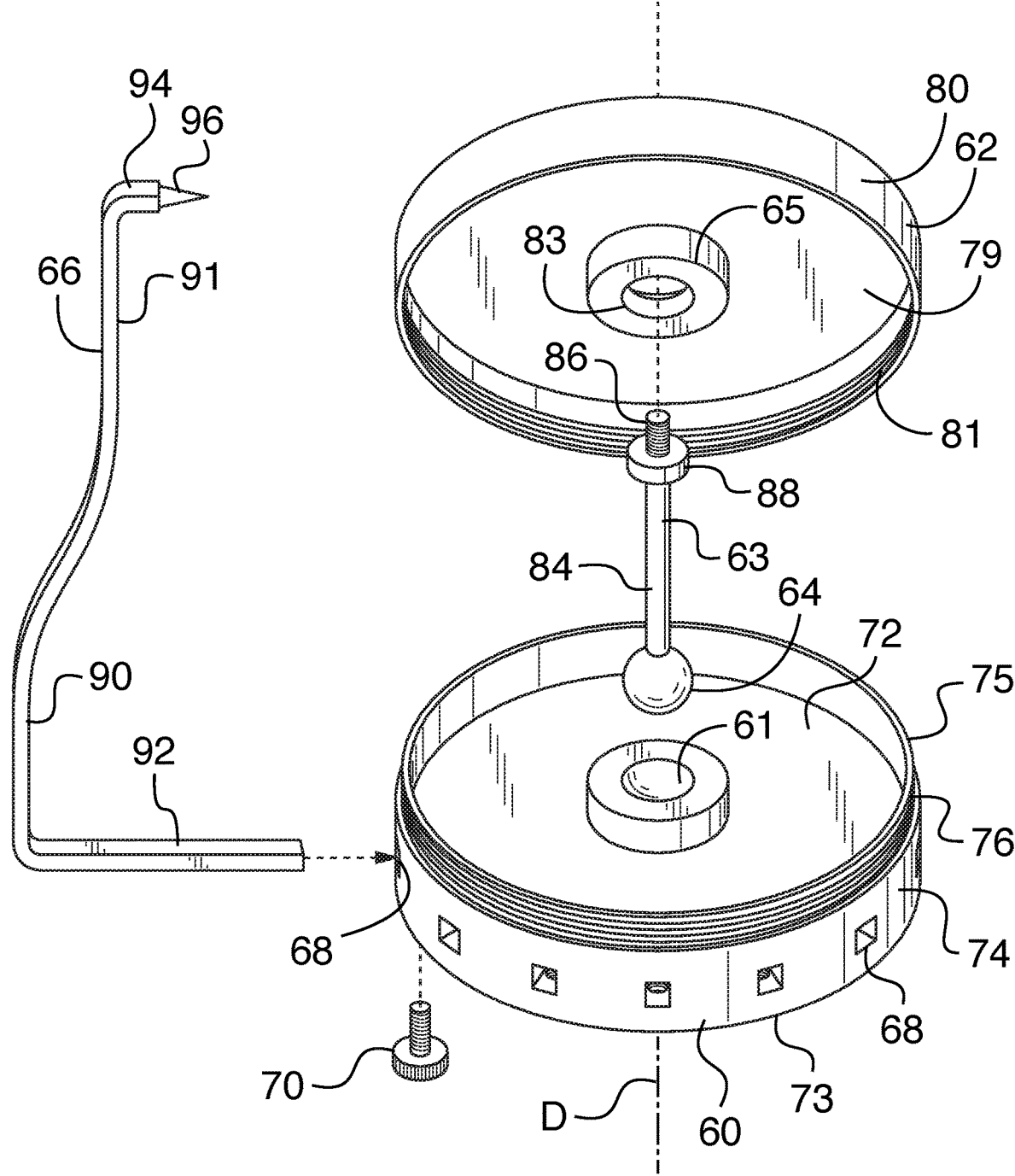
FIG. 3 is an exploded view of a fracture alignment portion of the instrument of FIG. 1.

The fracture alignment portion 14, which is best shown in FIG. 3, generally comprises a base 60 having a socket 61, a lid 62 having a socket 65, the lid 62 being adjustably connected to the base 60, a ball shaft 63 having a ball 64 at its end for engaging the sockets 61 and 65 to form a ball and socket joint, and a series of pointed tines 66 that are removably mounted within apertures 68 formed in the base 60 by fasteners 70.

Referring now to the individual features of the fracture alignment portion 14, the base 60 is a cylindrical body having a top surface 72, a bottom surface 73 opposite the top surface 72, and a side wall 74 extending between the top surface 71 and the bottom surface 73. A lip 75 extends upwardly from the top surface 72 forming part of the side wall 74. Mechanical threads 76 are provided on the outer circumference of the lip 75. The socket 61 is an annulus having an opened defined at its center that is aligned with the longitudinal axis D of the base 60. The socket 61 protrudes from the top surface 72 to a height that is less than the height of the lip 75 (i.e., the socket 61 is recessed relative to the lip 75).

A series of rectangular shaped apertures 68 are defined along the perimeter of the side wall 74. Each aperture 68 is normal to axis D and extends in a direction toward the axis D. A series of holes 78 (FIG. 6) extending parallel to axis D are defined on the bottom surface 73 of the base 60. Each hole 78 intersects one of the apertures 68, as shown in FIG. 1. A fastener 70 is configured to be mounted in one of the holes 78 for securing a tine 66 in the aperture 68 that intersects said one of the holes 78.

The lid 62 is a cylindrical member having a top exterior facing surface 77 (FIG. 1), a bottom interior facing surface 79 (i.e., facing the base 60) opposite the top surface 77, and a side wall 80 extending downward from the circumference of the bottom surface 79. Mechanical threads 81 are provided on the inner circumference of the wall 80. A socket 65 extends downwardly from the bottom surface 79 of the lid 62 (in the same direction as the wall 80). Like the socket 61, the socket 65 of the lid 62 is an annulus having an opening 83 defined at its center that is aligned with the longitudinal axis D of the base 60 in an assembled form of the fracture alignment portion 14. The opening 83 passes through the thickness of the lid 62 and is chamfered on the top surface 77 of the lid 62 to accommodate swiveling motion of the shaft 63. The socket 65 protrudes from the bottom surface 79 to a height that is less than the height of the wall 80 (i.e., the socket 65 is recessed relative to the wall 80).

The ball shaft 63 includes a shaft 84, a ball 64 disposed at the proximal end of the shaft 84, mechanical threads 86 at the distal end of the shaft 84 and a flange 86 positioned adjacent and proximally of the threads 86. The ball 64 is sized to be seated between the sockets 61 and 65 to form a ball and socket joint. The ball 64 is capable of swiveling on the sockets 61 and 65.

A plurality of tines 66 (one shown) are configured to be mounted within the apertures 68 of the base 60, as described above. Each tine 66 comprises a thin elongated member having a rectangular or square cross-section. The elongated member 60 includes an intermediate section 90 having a pre-determined length, a proximal end 92 that extends orthogonally relative to the section 90 (i.e., toward axis D), and a distal end 94 that also extends orthogonally relative to the section 90 in the same direction as the proximal end 92. The cross-sectional shape of the proximal end 92 compliments the shape of the aperture 68 in which the tine 66 is inserted. The distal portion 91 of the intermediate section 90 is bent toward the axis D.

A sharp and pointed spike 96 is formed at the distal end 94 of the tine 66. As best shown in FIG. 13, the spike 96 has a threaded post 97 that is configured to be threadedly engaged with an opening 98 that is formed at the distal end 94 of the tine 66. Alternatively, the spike 96 may be integrated with the tine 66.

According to another embodiment of the tine 66' shown in FIGS. 14 and 15, a clamp 67 is mounted to the distal end 94' of the tine 66'. More particularly, the clamp 67 has a threaded post 97' that is configured to be threadedly engaged with an opening 98' that is formed at the distal end 94' of the tine 66'. The clamp 67 includes a rounded semi-cylindrical surface 67a that is configured to contact the bone 104 without puncturing the bone 104. The clamp 67 and the spike 96 may be used interchangeably on the instrument 10.

In an assembled form of the fracture alignment portion 14, a plurality of tines 66 (preferably at least three, and more preferably four) are fixedly mounted within apertures 68 of the base 60 by separate fasteners 70. At least three tines 66 are required to sufficient constrain the bone 104 to which the tines 66 are attached. The tines 66 may be evenly spaced apart by 90 degrees about the circumference of the base 60, for example. The threads 81 of the lid 62 are mounted to the threads 76 of the base 60, and the ball 64 of the ball shaft 63 is captivated between the sockets 61 and 65. The threaded end 86 of the ball shaft 63 protrudes from the top end of the lid 62. It should be understood that the lid 62 may be mounted to the base 60 in other ways, such as by a clip, a clamp, a magnet, a ratchet, a bolt, a screw, a fastener, and so forth.

Although only one tine 66 and one fastener 70 are shown in FIG. 3, it should be understood that the instrument preferably has four tines 66 and four fasteners 70. However, the instrument may have any number of tines 66 and corresponding fasteners 70.

FIGS. 5-12 depicts a process for aligning a fracture and applying plates to the aligned fracture. It should be understood that the description that follows is not limited to any particular step or sequence of steps. The steps may be performed out of order.

Turning now to assembly and operation of the instrument 10, the rod 100 is positioned within holes formed in the medullary cavity of a femur bone 104 and a femoral implant 106 that is fixed to a distal portion 104b of the bone 104. A periprosthetic fracture 110 separates the distal portion 104b of the bone 104 from a proximal portion 104a of the bone 104. The details of the rod 100 and the femoral implant 106 are disclosed in U.S. Pat. No. 9,463,053 to Garino. It should be understood that the instrument 10 is not limited for use with a femur.

The instrument 10 is then ready for connection to the rod 100. As shown in FIG. 5, the threaded shaft 24 of the plate compression portion 12 is first threaded onto a threaded hole 102 formed at a distal end of an intramedullary rod 100 until the connector 16 abuts the distal end of the rod 100. The male threads on the threaded shaft 24 and the female threads in the threaded hole 102 are tailored such that, once the shaft 24 is connected to the hole 102, each hole 56 of one plate 55a registers both axially and radially with one hole 118 in the rod 100, and another hole 56 in the opposite plate 55b. Indicia in the form of markings may be provided on (i) the connector 16 at a location adjacent the shaft, and (ii) the distal end of the rod 100, to ensure proper radial alignment between the connector 16 and the rod 100.

Turning now to FIG. 6, the threaded shaft 86 of the fracture alignment portion 14 is then threadedly connected to the threaded hole 20 of the connector 16 of the plate compression portion 12 until the flange 88 abuts the lower surface of the connector 16. It should be understood that the threaded connections between the male shafts and female holes described above may be reversed without departing from the scope of the invention. For example, the shaft 24 of the connector 16 may include a threaded hole that is threaded onto a threaded post on the end of the rod 100. Alternatively, the threaded connections may be replaced with slotted connections to ensure proper radial and axial alignment.

Turning now to FIG. 7, the individual tines 66 (preferably at least four) of the fracture alignment portion 14 are slid toward the distal portion 104b of the bone 104. As the tines 66 are translated toward the bone 104, the proximal end 92 of each tine 66 slides within its respective aperture 68 in the base 60 until the spike 96 at the distal end of the tine 66 contacts the fractured distal portion 104b of the bone 104. It is noted that the tines 66 are adjustable so that they can conform to various patient anatomies.

Thereafter, the fasteners 70 at the bottom of the base 60 are rotated to lock the tines 66 in a fixed position relative to the base 60. The physician may hammer the distal end of each tine 66 to embed the spikes 96 into the fractured bone 104b. Thereafter, the base 60, the tines 66 and the fractured bone 104b (along with the implant 106) are interconnected.

Turning now to FIG. 8, at this stage of operation, the lid 62 is loosely connected to the base 60 such that the base 60 and the lid 62 are capable of pivoting with respect to the ball shaft 63. Pivoting is possible because the ball 64 of the ball shaft 63 is not compressed to any significant degree between the sockets 61 and 65.

The physician then pivots the base 60, the lid 62 and the tines 66 together, by an angle E (for example), in order to set the fracture 110 of the bone 104. The base 60, the lid 62, the tines 66 and the bone 104b pivot together and relative to the ball shaft 63. The ball shaft 63 cannot rotate relative to the bone 104 because the ball shaft 63 is connected to the connector 16, which is connected to the rod 100, which is connected through the bone 104. Compare the fracture 110 shown in FIG. 7 with the set fracture 110 shown in FIG. 8.

Turning now to FIG. 9, once the fracture 110 is properly set, the fracture alignment portion 14 is locked in position with respect to the rod 100. More particularly, the threaded portion of the lid 62 is rotated onto the threads 76 of the base 60 (as indicated by the arrow) thereby compressing the ball 64 of the ball shaft 63 between the sockets 61 and 65. Once the lid 62 is sufficiently secured to the base 60, the base 60 and the lid 62 cannot be moved relative to the ball shaft 63. At this point, the base 60, the lid 62, the tines 66, the ball shaft 63, the connector 16, the rod 100 and the entire bone 104 are interconnected. At this stage of operation, the distal portion 104b of the bone 104 is fixed relative to the rod 100 and the proximal portion 104a of the bone 104.

Turning now to FIG. 10, now that the fracture 110 is set, the physician rotates the fastener 30, thereby simultaneously rotating both gears 34 and 40 that are connected to the fastener 30. As described above, the teeth of the gear 34 are meshed with teeth 50a of the plate carrier 44a, whereas the teeth of the gear 40 are meshed with teeth 50b of the plate carrier 44b.

Rotation of the gear 34 in the clockwise direction (as shown by the arrow) causes the plate carrier 44a to translate inwardly toward the bone 104 as the teeth on the rotating gear 34 drive the teeth 50a of plate carrier 44a. More specifically, the first elongated portion 46 of the plate carrier 44a travels within the channel 28 of the connector 16 as the second elongated portion 52 moves the plate 55 that is connected thereto toward the bone 104.

Simultaneous rotation of the gear 40 in the clockwise direction (as viewed from the perspective of FIG. 10) causes the plate carrier 44b to translate inwardly toward the bone 104 as the teeth on the rotating gear 40 drive the teeth 50b of plate carrier 44b. The first elongated portion 46 of the plate carrier 44b travels within the channel 28 of the connector 16 as the second elongated portion 52 moves the plate 55 that is connected thereto toward the bone 104. This process is continued until the plates 55 are firmly positioned against the bone 104. As noted above, the holes 56 in the plates 55 and the holes 118 in the rod 100 are already in axial and radial alignment at this stage of the process.

The physician then positions a drill in one of the holes 56 in plate 55a, and drills a hole in the portion of bone 104 between the rod 100 and the plate 55a. The drill bit passes through one of the holes 118 in the rod 100, and continues to drill a hole in the portion of bone 104 between the rod 100 and the plate 55b. The drill bit eventually protrudes through one of the holes 56 in plate 55b. The drill bit is then removed. As will be described hereinafter, a transfixing bolt 116 is then positioned through the straight hole that was formed by the drill bit for securing the plates 55 to the bone 104. The aforementioned drilling step is repeated for each bolt 116 that is used to secure the plates 55 to the bone 104.

A plurality of transfixing bolts 116 (one shown protruding from plate 55) are used to fix the plates 55 to the bone 104 and the rod 100, thereby compressing the aligned fracture 110. Each transfixing bolt 116 (one shown) is positioned through a respective hole 56 in the plate 55a, through a respective transverse hole 118 (FIG. 7) in the rod 100, and through a respective hole 56 in the plate 55b. The free end of the bolt 116 is mounted to the outside of the plate 55b by a nut 117. Further details of the process for using transfixing bolts 116 to fix the plates 55 to the bone 104 and the rod 100 are described in U.S. Pat. No. 9,463,053 to Garino. As another example, a transfixing screw may be positioned through a respective hole 56 in one of the plates 55, through a respective transverse hole 118 in the rod 100, and embedded into the bone 104. It should be understood that various ways exist for attaching a plate to the rod, and the invention is not limited to any particular mounting process.

At this stage, the plates 55 are fixed to the bone 104 and the rod 100, and the fracture 110 is stabilized. The instrument 10 can now be removed from the bone 104.

Turning now to FIG. 11, to remove the instrument 10 from the bone 104, the tines 66 are first removed from the bone 104 using either a hammer or the physician's hand to remove the spikes 96 from the bone 104. The fasteners 70 are loosened and the tines 66 may be removed from the instrument 10, if so desired. The fastener 30 is then rotated in a counter-clockwise direction (as depicted by the arrow), thereby causing the plate carriers 44a and 44b to move outwardly (by virtue of the previously described geared arrangement) and separate from the plates 55. The entire instrument 10 is then disconnected from the rod 100 by rotating the instrument 10 to disengage the threaded shaft 24 from the threaded hole 102 of the rod 100. The instrument 10 may then be withdrawn and completely removed from the bone 104. FIG. 12 depicts the bone 104 with the plates 55 applied thereto.

While preferred embodiments of the invention have been shown and described herein, it will be understood that such embodiments are provided by way of example only. For example, in lieu of the threaded connections described herein, those connections may be replaced by a clip, a clamp, a magnet, a ratchet, a bolt, a screw, a fastener, and so forth. Numerous variations, changes, and substitutions may occur to those skilled in the art without departing from the spirit of the invention. Accordingly, it is intended that the appended claims cover all such variations that fall within the spirit and scope of the invention.

What is claimed is:

1. An instrument for setting a fracture in a bone and affixing a bone plate to the fractured bone with a connection to an intramedullary rod fixed in the fractured bone, said instrument comprising:
   a connector for directly connecting the instrument to the intramedullary rod,
   at least two tines extending forward of the connector, each tine having a distal end configured to contact the bone, the tines each being movably connected to the connector to move laterally with respect to longitudinal axes of the connector and the intramedullary rod for orienting the fractured bone with respect to the intramedullary rod, each tine being independently movable in a lateral direction with respect to the connector and the other tine of the at least two tines; and at least one plate carrier configured to receive the bone plate, the at least one plate carrier movably connected to the connector and configured to move relative to the connector and the tines to position the bone plate adjacent the bone in a predetermined alignment with the intramedullary rod.

2. The instrument of claim 1, wherein the instrument comprises a plate compression portion that is connected to a fracture alignment portion, wherein the tines form part of the fracture alignment portion, the at least one plate carrier forms part of the plate compression portion, and the connector connects the plate compression portion to the fracture alignment portion.

3. The instrument of claim 2, wherein the connection between the plate compression portion and the fracture alignment portion is a swivel connection configured to permit the fracture alignment portion to swivel relative to the plate compression portion.

4. The instrument of claim 2, wherein the fracture alignment portion includes a base to which the at least two tines are mounted, a lid releasably connected to the base, a base socket disposed on the base, a lid socket disposed on the lid, and a ball shaft comprising a ball end positioned between the base socket and the lid socket, wherein the ball shaft is configured to swivel relative to the base socket and the lid socket.

5. The instrument of claim 4, wherein the lid is adjustably mounted to the base and is configured to adjustably compress the ball between the sockets.

6. The instrument of claim 4, wherein the tines further comprise a proximal end connected to the base, the base having apertures configured to receive the proximal ends of the tines, wherein the proximal ends of the tines are axially movably positioned within the apertures.

7. The instrument of claim 6, further comprising fasteners for locking a position of the tines to the base.

8. The instrument of claim 4, wherein the ball shaft includes a distal end opposite the ball end, the distal end attached to the connector.

9. The instrument of claim 8, wherein the distal end of the ball shaft is threaded and is configured to be threadably connected to a mating threaded end of the connector.

10. The instrument of claim 1, wherein each tine includes one of: a spike configured to be embedded into the bone, or a clamp configured to be positioned against the bone.

11. The instrument of claim 1, wherein the connector includes a threaded post for connecting to a threaded hole in the intramedullary rod.

12. The instrument of claim 1 further comprising a second plate carrier, each plate carrier slidably connected to the connector and configured to be connected to an individual bone plate.

13. The instrument of claim 12, wherein each plate carrier includes gear teeth meshed with a gear on a rotatable shaft mounted to the connector such that rotation of the shaft causes simultaneous translation of the plate carriers.

14. The instrument of claim 12, wherein the plate carriers are each mounted in a channel disposed in the connector.

15. A method of using an instrument to mend a fracture in a bone comprising:

(i) directly attaching a connector of the instrument to an intramedullary rod positioned within a cavity of the bone;

(ii) moving a plurality of tines, which extend forward of the connector, in a lateral direction with respect to longitudinal axes of the intramedullary rod and the connector to position the plurality of tines of the instrument against the bone, each tine being independently positionable in the lateral direction against the bone with respect to the intramedullary rod and the other tines of the plurality of tines;

(iii) moving the tines in the lateral direction with respect to the intramedullary rod and the connector to orient the fractured bone with respect to the intramedullary rod thereby setting the fracture; and (iv) moving a first plate carrier with respect to the intramedullary rod to position a first plate, which is mounted to the first plate carrier, against a first surface of the bone in alignment with the intramedullary rod.

16. The method of claim 15 further comprising inserting the intramedullary rod into a medullary cavity of the bone.

17. The method of claim 16 further comprising inserting a fastener through a hole in the plate and a hole in the intramedullary rod.

18. The method of claim 16 further comprising the step of (v) moving a second plate carrier with respect to the intramedullary rod to position a second plate, which is mounted to the second plate carrier, against a second surface of the bone.

19. The method of claim 18, wherein the step of moving the first plate carrier and the step of moving the second plate carrier are performed simultaneously by adjusting a fastener connected to both the first and second plate carriers through a geared arrangement.

20. The method of claim 16 further comprising locking the tines in a fixed position with respect to the connector and the intramedullary rod once the fracture is set.

21. The method of claim 16, wherein holes in the first plate are axially and radially aligned with corresponding holes in the intramedullary rod.

22. A method of using an instrument to mend a fracture in a fractured bone comprising:

(i) attaching the instrument to an intramedullary rod positioned within a cavity of the fractured bone using a connector;

(ii) moving a fracture alignment portion of the instrument, which extends forward of the connector, against the fractured bone;

(iii) moving the fracture alignment portion in a lateral direction with respect to a longitudinal axis of the intramedullary rod to orient the fractured bone with respect to the intramedullary rod, and thereby setting the fracture;

(iv) following step (iii), moving a first plate carrier with respect to the intramedullary rod to position a first plate, which is mounted to the first plate carrier, against a first surface of the fractured bone in alignment with the intramedullary rod;

(v) moving a second plate carrier with respect to the intramedullary rod to position a second plate, which is mounted to the second plate carrier, against a second surface of the fractured bone in alignment with the intramedullary rod; and (vi) delivering a fastener in the lateral direction through openings in the first plate carrier, the intramedullary rod and the second plate carrier thereby locking the plates, the fractured bone and the intramedullary rod together.

\* \* \* \* \*

UNITED STATES PATENT AND TRADEMARK OFFICE
CERTIFICATE OF CORRECTION

PATENT NO. : 10,610,274 B2
APPLICATION NO. : 15/906490
DATED : April 7, 2020
INVENTOR(S) : Jonathan P. Garino Page 1 of 1

It is certified that error appears in the above-identified patent and that said Letters Patent is hereby corrected as shown below:

In the Claims

In Column 9, Claim 6, Lines 40 and 41, "the tines are axially movably positioned" should read – the tines are movably positioned –

Signed and Sealed this
Tenth Day of November, 2020

Andrei Iancu
*Director of the United States Patent and Trademark Office*